US007320777B2

(12) United States Patent
Bordenkircher et al.

(10) Patent No.: US 7,320,777 B2
(45) **Date of Patent: *Jan. 22, 2008**

(54) PCR SAMPLE HANDLING DEVICE

(75) Inventors: Gary L. Bordenkircher, Livermore, CA (US); Gary Lim, San Francisco, CA (US); Jacob Koppel Freudenthal, Alameda, CA (US)

(73) Assignee: Applera Corporation, Foster City, CA (US)

( * ) Notice: Subject to any disclaimer, the term of this patent is extended or adjusted under 35 U.S.C. 154(b) by 518 days.

This patent is subject to a terminal disclaimer.

(21) Appl. No.: 10/301,870

(22) Filed: Nov. 22, 2002

(65) Prior Publication Data

US 2003/0124714 A1 Jul. 3, 2003

Related U.S. Application Data

(63) Continuation of application No. 09/897,500, filed on Jul. 3, 2001, now Pat. No. 6,514,750.

(51) Int. Cl.
*B01L 9/00* (2006.01)
*C12M 1/34* (2006.01)

(52) U.S. Cl. ................ 422/104; 435/287.2; 435/288.4; 435/809

(58) Field of Classification Search .................. 422/50, 422/68.1, 102, 104; 435/286.2, 287.2, 288.4, 435/288.7, 809, 810
See application file for complete search history.

(56) References Cited

U.S. PATENT DOCUMENTS

| | | | |
|---|---|---|---|
| 3,080,759 A | 3/1963 | McQuaid | |
| 3,933,165 A | 1/1976 | Budzak et al. | |
| 4,948,564 A | 8/1990 | Root et al. | 422/101 |
| 5,210,015 A | 5/1993 | Gelfand et al. | 435/6 |
| 5,456,360 A | 10/1995 | Griffin | |

(Continued)

FOREIGN PATENT DOCUMENTS

| | | |
|---|---|---|
| DE | 197 39 119 A1 | 3/1999 |

(Continued)

OTHER PUBLICATIONS

U. Landegren et al., "A Ligase-Mediated Gene Detection Technique," *Science*; 241:1077-80 (Aug. 1988).

(Continued)

*Primary Examiner*—David Redding
(74) *Attorney, Agent, or Firm*—Finnegan, Henderson, Farabow, Garrett & Dunner, L.L.P.

(57) ABSTRACT

A device for handling PCR microcards, each having an array of sample chambers closed by a transparent material on one side thereof, in relation to a PCR instrument, the device including a carrier having an apertured region with an array of holes corresponding in number and relative location with the array of sample chambers in each of the microcards, and a provision for retaining a microcard on the carrier so that the transparent material faces the apertured region with the reagent sample chambers aligned, respectively, with the holes in the apertured region, and so that the side of the microcard opposite the transparent material is unobstructed at least throughout the array of sample chambers. The device cooperates with the PCR instrument to ensure accurate positioning of the carrier and the microcard retained thereon for real time PCR processing.

43 Claims, 6 Drawing Sheets

U.S. PATENT DOCUMENTS

| | | | | |
|---|---|---|---|---|
| 5,538,848 | A | 7/1996 | Livak et al. | 435/5 |
| 5,710,381 | A | 1/1998 | Atwood et al. | |
| 5,779,981 | A | 7/1998 | Danssaert et al. | |
| 5,780,717 | A | 7/1998 | Wise et al. | 73/23.2 |
| 5,928,907 | A | 7/1999 | Woudenberg et al. | 435/91.2 |
| 6,015,674 | A | 1/2000 | Woudenberg et al. | 435/6 |
| 6,159,368 | A | 12/2000 | Moring et al. | 210/321.75 |
| 6,251,343 | B1 | 6/2001 | Dubrow et al. | |
| 6,272,939 | B1 | 8/2001 | Frye et al. | 73/864.81 |
| 6,514,750 | B2 * | 2/2003 | Bordenkircher et al. | 435/286.2 |
| 2002/0001848 | A1 | 1/2002 | Bedingham et al. | |
| 2002/0047003 | A1 | 4/2002 | Bedingham et al. | |
| 2002/0048533 | A1 | 4/2002 | Harms et al. | |
| 2002/0064885 | A1 | 5/2002 | Bedingham et al. | |

FOREIGN PATENT DOCUMENTS

| | | | |
|---|---|---|---|
| EP | 0 895 240 | A1 | 2/1999 |
| EP | 0 955 097 | A1 | 11/1999 |
| EP | 1 088 590 | A1 | 4/2001 |
| WO | WO91/17239 | | 11/1991 |
| WO | WO97/36681 | | 10/1997 |
| WO | WO 01/28684 | A2 | 4/2001 |
| WO | WO 01/56697 | A | 8/2001 |
| WO | WO 02/01180 | A2 | 1/2002 |
| WO | WO 02/01181 | A2 | 1/2002 |

OTHER PUBLICATIONS

D. Nickerson et al., "Automated DNA diagnostics using an ELISA-based oligonucleotide ligation assay," *Proc. Natl. Acad. Sci USA*, 87:8923-27 (Nov. 1990).

P. Grossman et al., "High-density multiplex detection of nucleic acid sequences: oligonucleotide ligation assay and sequence-coded separation," *Nucl. Acids Res.*, 22:4527-34 (1994).

Co-pending U.S. Appl. No. 09/496,408, Inventors: Hon Shin et al., filed Feb. 2, 2000 Title: Apparatus and method for ejecting sample well trays.

Co-pending U.S. Appl. No. 09/848,270, Inventors: Frye et al., filed May 4, 2001 Title: System and method for filling a substrate with a liquid sample.

Co-pending U.S. Appl. No. 09/977,225, Inventors: Freudenthal et al., filed Oct. 16, 2001 Title: System for filling substrate chambers with liquid.

Co-pending U.S. Appl. No. 09/606,006, Inventors: Barzilai et al., filed Jun. 29, 2000 Title: Apparatus and method for transporting sample well trays.

* cited by examiner

FIG. 3
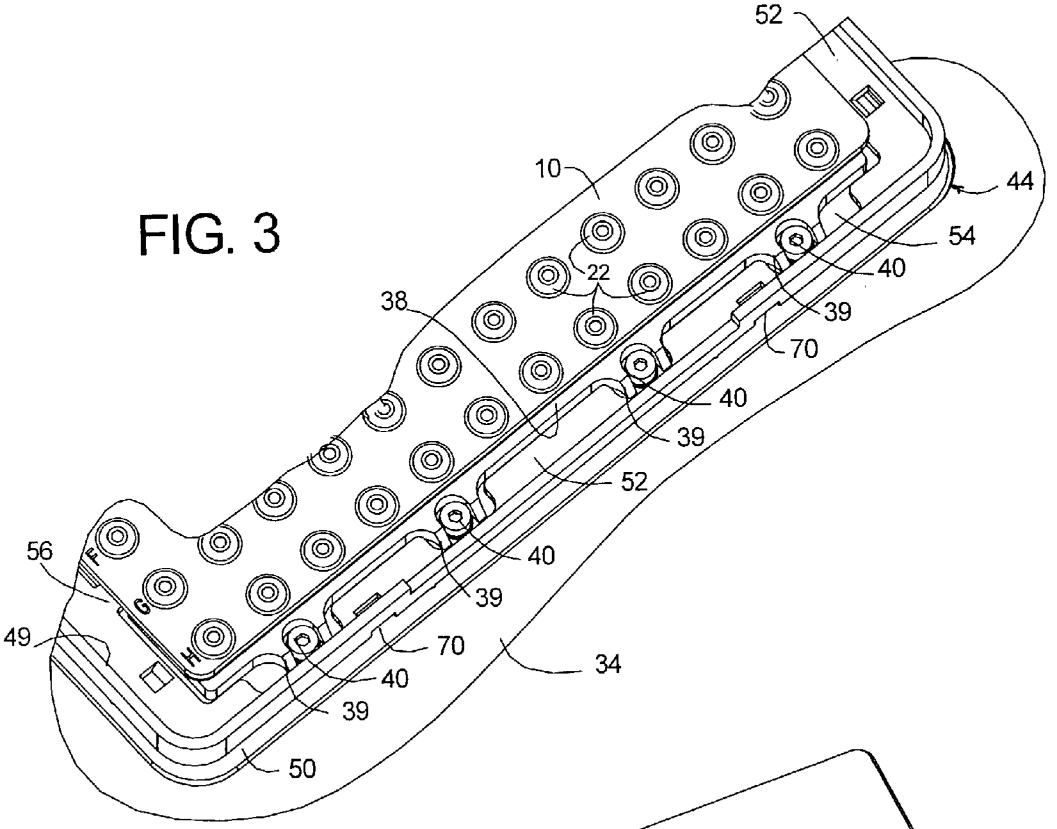
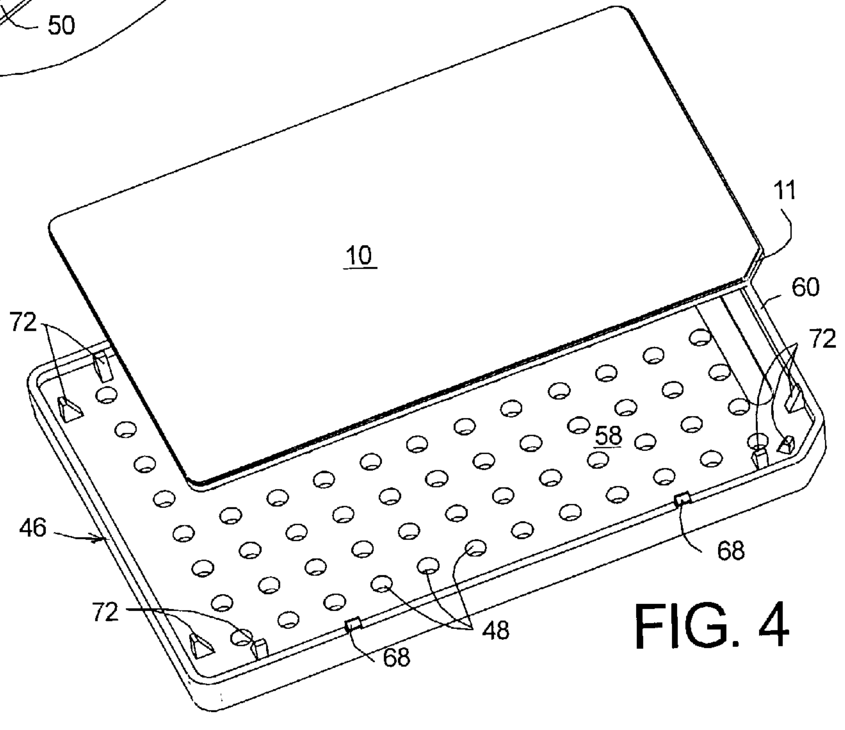
FIG. 4

FIG. 5A
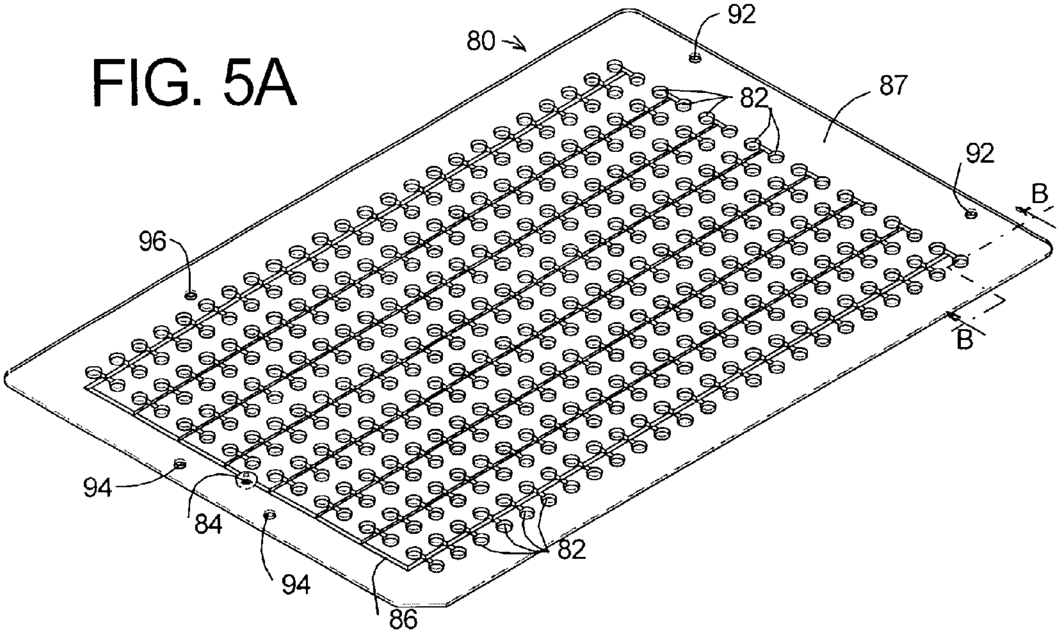
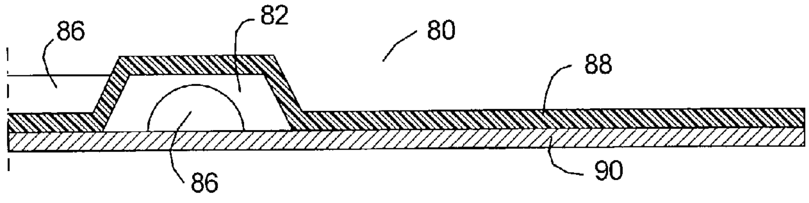
FIG. 5B

PCR SAMPLE HANDLING DEVICE

This application is a continuation of application Ser. No. 09/897,500, filed Jul. 3, 2001, now U.S. Pat. No. 6,514,750, which is incorporated herein by reference.

BACKGROUND OF THE INVENTION

1. Field of the Invention

The present invention relates to apparatus for handling microcards used for performing polymerase chain reactions (PCR), for example, and, more particularly, to a device for positioning such microcards in relation to a PCR instrument.

2. Description of the Related Art

A substrate for simultaneously testing a large number of analytes, which has a small sample size and a large number of detection chambers, has been described in published PCT International Application, WO97/36681, assigned to the assignee of the present application, the contents of which are hereby incorporated by reference herein. Also, in commonly assigned U.S. patent application Ser. No. 09/549,382, filed Apr. 13, 2000, now U.S. Pat. No. 6,272,939, the complete disclosure of which is incorporated by reference, a further development of a card-like substrate member having a plurality of sample detection chambers is disclosed together with a system for filling the member with a liquid sample to react with reagents located in the sample detection chambers during thermal cycling of a PCR process. Such card-like substrate members are a spatial variant of the micro-liter plate and are referred to hereinafter as "microcards." However, the microcards are often referred to in the art as "consumables" because they are relatively inexpensive and disposable after use, and as such, may be made from a variety of different materials and may assume different shapes and sizes.

Microcards typically contain 96, 384, or more, individual sample chambers, each having a volume of about 1.0 μL or less in a card size of 7 cm×11 cm×0.2 cm, for example. Although both the number of sample chambers and the volume size of the individual sample chambers may vary widely, the relatively small size of the microcards present problems in transporting them into and out of a PCR instrument, such as instrument models 7700 or 7900HT available from Applied Biosystems of Foster City, Calif., and aligning the microcard with a thermal cycling block and an optical system in the PCR instrument.

Handling, including placing and removing microcards into and from thermal cyclers of a PCR instrument, storing, and transporting of the microcards may be accomplished either manually or robotically. A robot typically functions by gripping the sides of the microcard by "fingers", or grips. Because a microcard may have a relatively thin body, with side edges as thin as 0.5 mm or less in thickness, robotic handling may become impractical or inconsistent, especially when multiple microcards are stacked together. Additionally, to accomplish real time PCR processing the microcard must be aligned with an optical reading device, such as a CCD or laser scanner. To be effective, such alignment requires high precision usually greater than tolerances provided by the edges of the microcard. There is a need for reliable alignment of a microcard with a scanner, camera, or luminometer of a PCR instrument.

In addition to the problems associated with alignment, PCR processing requires uniform and complete contact of the sample chambers of the microcard with a thermal cycling block of a PCR instrument. In some instances, where the microcard is formed by laminated plastic materials, there is a tendency for warpage of the card from an initial planar configuration. Thus, to ensure complete contact of the sample chambers of the microcard with the surface of the thermal cycling block, a flexing of the microcard is required so that is conforms to the typically planar surface of that block. In other instances, the microcard may be formed of flexible material incapable, in itself, to maintain a shape that conforms to the surface of the thermal cycling block. In positioning the latter types of microcards relative to the thermal cycling block of a PCR instrument, therefore, provision must be made to conform the microcard to the surface of the thermal cycling block.

Thus, it will be appreciated that there is a need for improvements in apparatus for positioning microcards of the types mentioned above in relation to a PCR instrument, and to facilitate handling of such microcards in general.

SUMMARY OF THE INVENTION

The advantages and purpose of the invention will be set forth in part in the description which follows, and in part will be obvious from the description, or may be learned by practice of the invention. The advantages and purpose of the invention will be realized and attained by means of the elements and combinations particularly pointed out in the appended claims.

To attain the advantages and in accordance with the purpose of the invention, as embodied and broadly described herein, the invention is directed to a device for handling PCR microcards, each having an array of sample chambers closed by a transparent material on one side thereof, in relation to a PCR instrument. The device includes a carrier having an apertured region with an array of holes corresponding in number and relative location with the array of sample chambers in each of the microcards, and a structure for retaining a microcard on the carrier so that the transparent material faces the apertured region with the sample chambers aligned, respectively, with the holes in the apertured region, and so that the side of the microcard opposite the transparent material is unobstructed at least throughout the array of sample chambers. Also structure is provided for positioning the microcard retained on the carrier in relation to the PCR instrument.

In another aspect, the advantages and purpose of the invention are attained by such a device having a carrier plate including the apertured region, and a peripherally closed retention frame having an opening at least as large as the array of sample chambers and being fitted to the carrier to retain the microcard in relation to the carrier plate.

In yet another aspect, the advantages and purpose of the invention are attained by such a device for a microcard that has through-holes in marginal portions thereof outside the array of sample chambers, a plate member including the apertured region, and pins projecting from the plate member outside of the apertured region to engage in the through-holes in the marginal areas of the microcard.

In a further aspect, the advantages and purpose of the invention are attained by a PCR kit including at least one handling device, a supply of microcards, and optionally, the appropriate thermal block for processing the supplied microcard. Other kits might include microcards filled with reagents of a supplier's design or custom reagents ordered by a customer. The appropriate handling device would be included with the filled microcards.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several exemplary embodiments of the invention and together with the description, serve to explain the principles of the invention. In the drawings.

FIG. 3 is an enlarged fragmentary perspective view of the embodiment shown in FIG. 2;

FIG. 4 is an exploded perspective view showing the bottom of the microcard of FIG. 1 in relation to a carrier component of the embodiment of FIG. 2;

FIG. 5A is a perspective view a flexible laminated foil microcard that may be used with the present invention;

FIG. 5B is an enlarged fragmentary cross section taken on line B—B of FIG. 5;

DESCRIPTION OF THE PREFERRED EMBODIMENTS

Reference will now be made in detail to the exemplary embodiments of the invention, examples of which are illustrated in the accompanying drawings. Wherever possible, the same reference numbers will be used throughout the drawings to refer to the same or like parts.

In accordance with the present invention, a device is provided for handling PCR microcards, each having an array of discreet reagent containing sample chambers closed by a transparent material on one side thereof, in relation to a PCR instrument. Each sample chamber preferably contains an analyte-specific reagent that reacts with a selected analyte that may be present in the liquid sample. The device is designed for retaining a micro-card on a carrier so that a transparent side of the microcard faces an apertured region of the carrier with the reagent sample chambers aligned, respectively, with the holes in the apertured region, and so that the opposite side of the microcard is unobstructed at least throughout the array of reagent containing sample chambers. As disclosed herein and shown in FIGS. 1A and 1B, one embodiment of the apparatus is particularly applicable to a microcard generally designated by the reference number 10.

Although the microcard 10 and a system for filling it with sample liquid is fully disclosed in the above cited U.S. patent application Ser. No. 09/549,382, filed Apr. 13, 2000, now U.S. Pat. No. 6,272,939, incorporated herein by reference, the features of the microcard 10 that are applicable to the apparatus of the present invention will be described below.

Figure 1A:
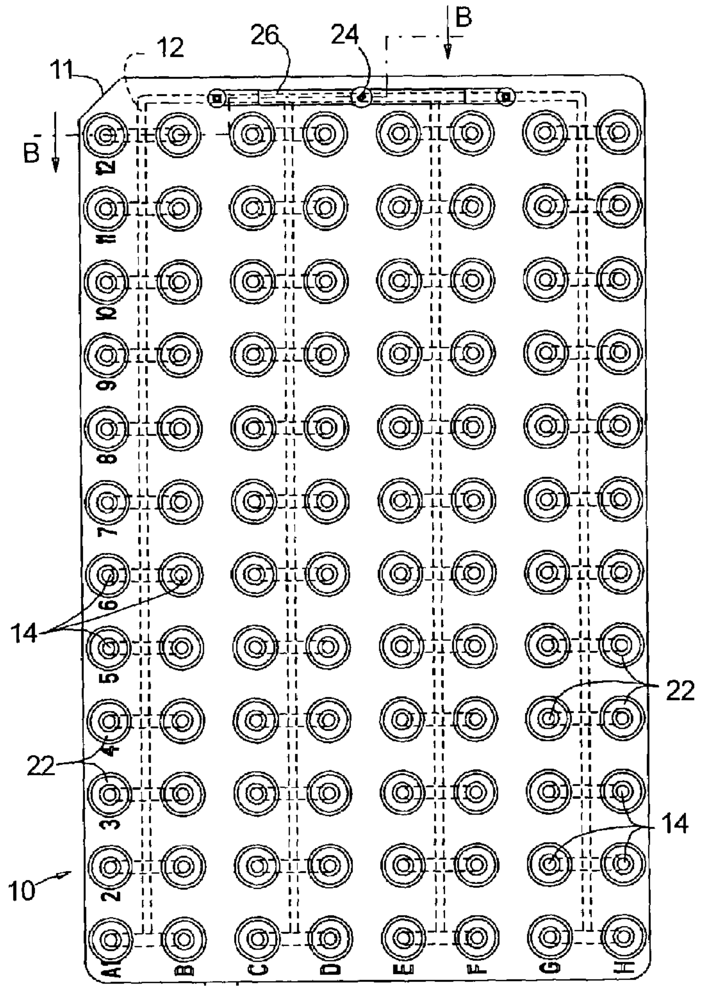
FIG. 1A is a top plan view of a laminated plastic microcard that may be used with the present invention.

The microcard 10 is formed by a laminated substrate shown in FIG. 1A as being generally rectangular in shape, but can be a variety of shapes and sizes, and in the illustrated embodiment, by way of example only, is approximately 7 cm×11 cm×0.2 cm. A chamfered corner 11 is provided to ensure proper orientation of the microcard with a PCR instrument. The microcard 10 defines a network 12 of passageways including a plurality of sample detection chambers 14. Each sample detection chamber can hold a predefined volume of liquid sample, such as, for example, approximately 1 μl. This volume can be varied depending on the specific application.

Figure 1B:
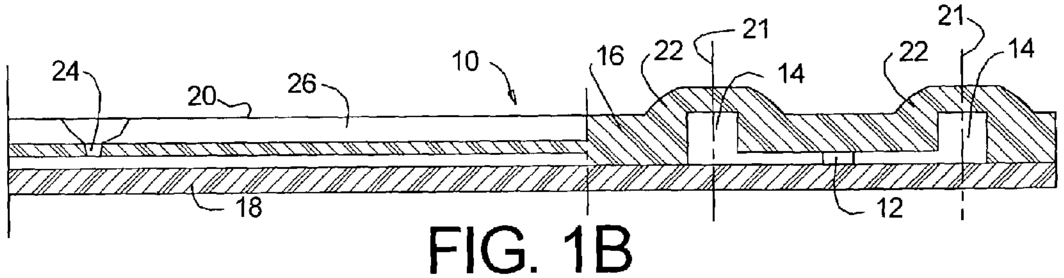
FIG. 1B is an enlarged fragmentary cross section on line B—B of FIG. 1A.

As embodied herein and shown in FIG. 1B, the microcard 10 is preferably formed as including a top plate 16 and a bottom plate 18. The top plate 16 has an upper surface 20 that contains raised surfaces 22. The raised surfaces 22 define the top portion of each sample detection chamber 14, and are tapered downwardly and outwardly in relation to a central axis 23 of each sample detection chamber 14. Preferably, the raised surfaces are those of truncated spheres, but other tapered surfaces, such as those of a cone or pyramid could be used.

The top and bottom plates 16 and 18 can be joined to each other by a variety of methods so that the network of passageways may be evacuated by a vacuum source, so that the liquid sample does not leak from the substrate, and to withstand temperature fluctuations that can occur during thermal cycling. Preferably, the plates 16 and 18 are joined using ultrasonic welding, but other suitable methods include the use of adhesives, pressure-sealing, or heat curing.

As embodied herein and shown in FIGS. 1A and 1B, the microcard 10 is provided with a sample inlet port 24 for the entrance of the liquid sample into the network 12 of passageways. The sample inlet port 24 is located preferably in the center of an attachment/bladder groove 26, in the top plate 16 of the microcard 10, and extends through the attachment/bladder groove 26. The attachment/bladder groove 26 extends across a portion of the width of the top surface of the substrate plate 16 in a region outside of the sample detection chambers 14 and has a top surface slightly recessed from the upper surface 20 of the top plate 16.

As described fully in the above-cited U.S. application Ser. No. 09/549,382, now U.S. Pat. No. 6,272,939, the attachment/bladder groove 26 provides an air pocket for the liquid sample in the network of passageways so that when the filled substrate undergoes temperature fluctuations during thermal cycling operations expansion of the liquid sample in the network 12 of passageways occurs without significantly increasing the pressure on the substrate. Also, the liquid sample may flow into the attachment/bladder groove 26 through sample port 24 under such conditions.

The top and bottom plates 16 and 18 may be made out of any suitable material that can be manufactured according to the required specifications, can withstand any temperature fluctuations that may later occur, i.e., during thermal cycling or other operations performed on the substrate, and can be suitably joined. In addition, for real time optical detection of liquid samples during thermal cycling, the top of each sample detection chamber 14 must be optically transparent for detection of the reaction. For this purpose, silica-based glasses, quartz, polycarbonate, or any optically transparent plastic layer, for example, may be used. For use in PCR reactions, the material should be PCR compatible, and the material should be preferably be substantially fluorescence free. In one embodiment, the material for the top plate is a polycarbonate manufactured by "BAYER"™, referred to as FCR 2458-1112 and the material for the bottom plate is a 0.015 inch thickness polycarbonate manufactured by "BAYER"™, referred to as Makrofol DE1-1D. The substrate plates can be formed by a variety of methods known in the art. For example, top plate 16 may be injection molded, whereas bottom plate 18 may be die-cut. Any other suitable method of manufacturing the plates is also acceptable.

Prior to assembly of the top and bottom plates 16 and 18, an analyte-specific reagent is typically placed in each detection chamber 14. One or more of the detection chambers may be left empty to function as a control. These analyte-specific reagents in the detection chambers may be adapted to detect a wide variety of analyte classes in the liquid sample, including polynucleotides, polypeptides, polysaccharides, and small molecule analytes, by way of example only. The polynucleotide analytes are detected by any suitable method, such as polymerase chain reaction, ligase chain reaction, oligonucleotide ligation assay, or hybridization assay. A preferred method of polynucleotide detection is the exonuclease assay referred to as "TAQMAN"™. Non-polynucleotide analytes may also be detected by any suitable method, such as antibody/antigen binding. The above detection methods are well-known in the art. They are described in detail in the following articles and patents: U.S. Pat. No. 5,210,015 of Gelfand et al.; U.S. Pat. No. 5,538,848 of Livak et al.; WO 91/17239 of Barany et al. published on Nov. 14, 1991; "A Ligase-Mediated Gene Detection Technique" by Landegren et al published in Science 241:1077–90 (1988); "High-density multiplex detection of nucleic acid sequences: oligonucleotide ligation assay and sequence-coded separation" by Grossman et al., published in Nucleic Acid Research 22:4527–34 (1994); and "Automated DNA diagnostics using an ELISA-based oligonucleotide ligation assay" by Nickerson et al., published in Proc. Natl. Acad. Sci. USA 87:8923–27 (1990).

Figure 2:
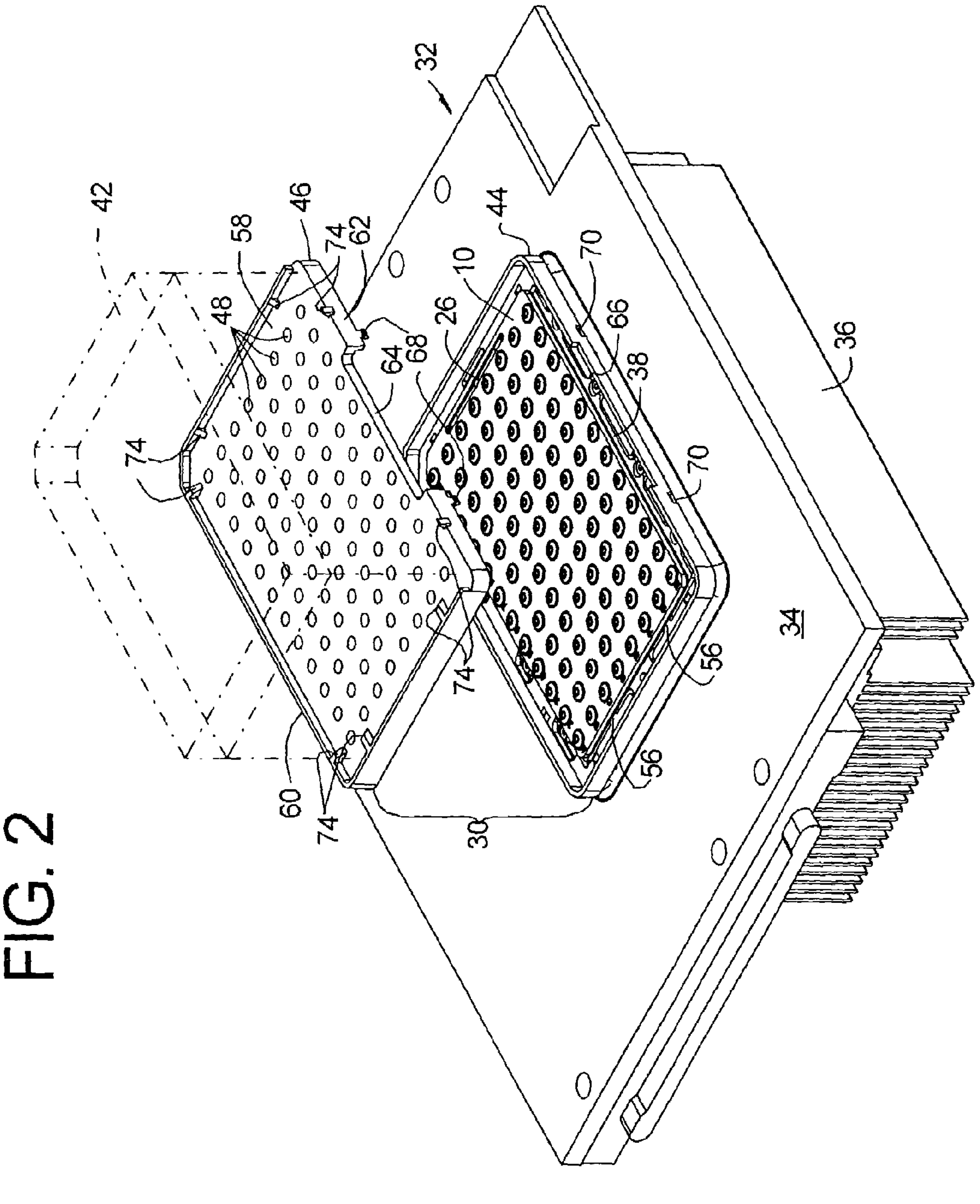
FIG. 2 is an exploded perspective view of an embodiment of the invention together with a thermal cycling device of a PCR instrument.
Figure 6A:
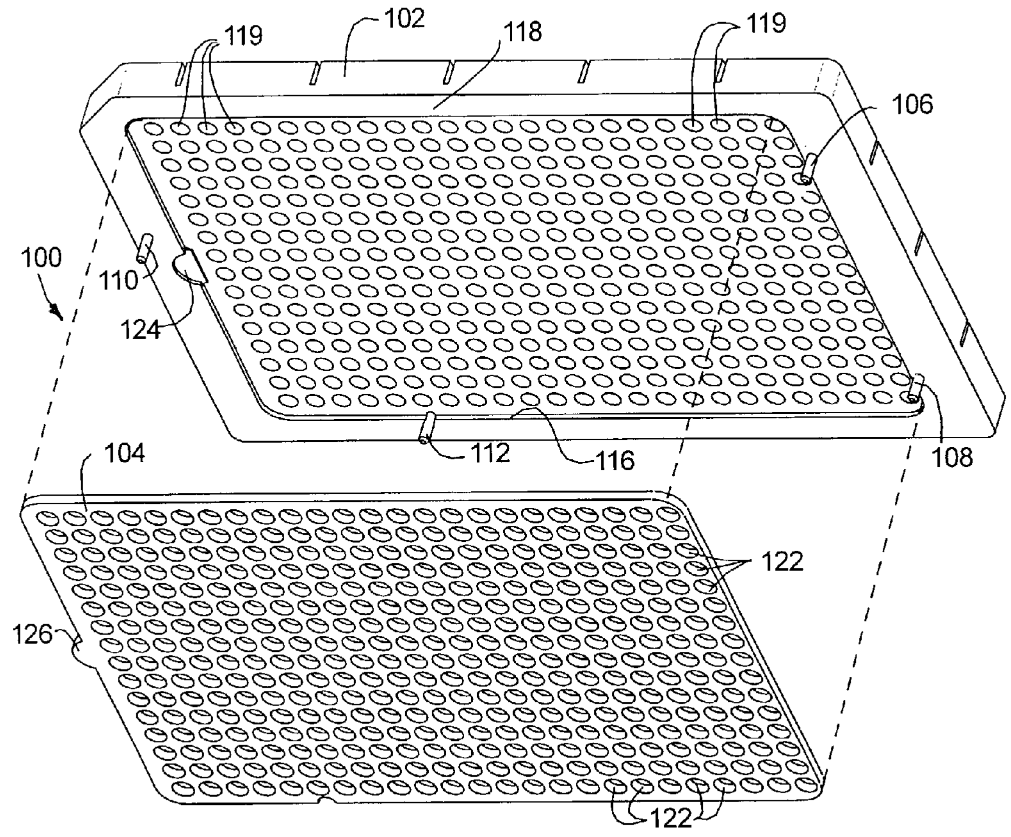
FIG. 6A is an exploded perspective view showing an alternative embodiment of the present invention for use with the microcard shown in FIG. 5.
Figure 6B:
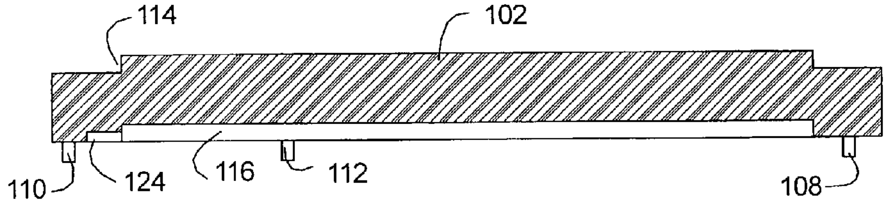
FIG. 6B is a longitudinal cross section taken through the carrier plate of FIG. 6A.
Figure 7:
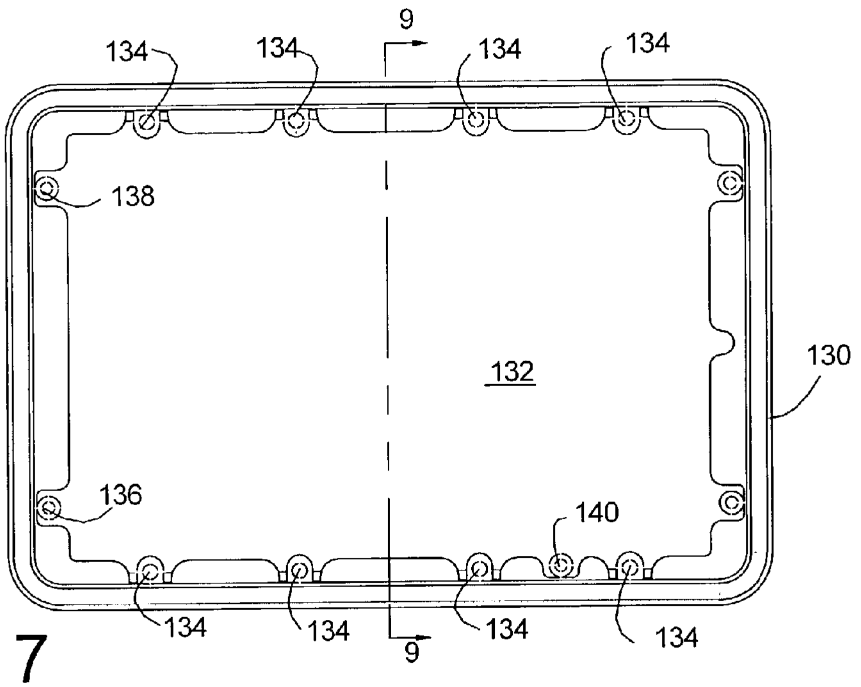
FIG. 7 is a plan view of a thermal cycling block used with the embodiment of FIG. 6.
Figure 8:
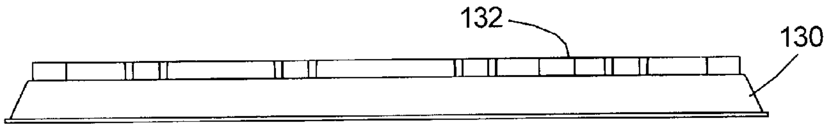
FIG. 8 is a side view of the thermal cycling block of FIG. 7.
Figure 9:
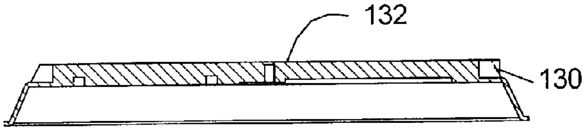
FIG. 9 is a cross section on line 9—9 of FIG. 7.
Figure 10:
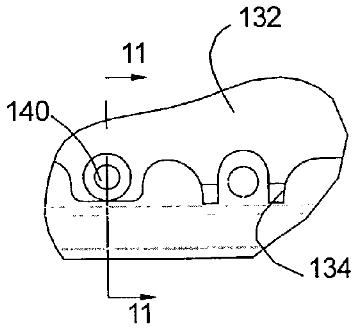
FIG. 10 is an enlarged fragmentary plan view of the thermal cycling block shown in FIG. 7.
Figure 11:
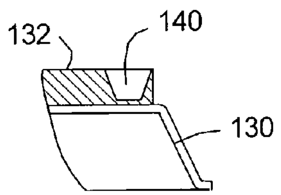
FIG. 11 is a cross section on line 11—11 in FIG. 10.

In FIG. 2, an embodiment of a handling device for the microcard 10 is designated generally by the reference number 30 and shown relative to a thermal cycling device 32 of a PCR instrument, such as models 7700 or 7900HT available from Applied Biosystems of Foster City, Calif. Such instruments are capable of automated PCR processing and include an optical system positioned above the thermal cycling device 32 for reading sample fluorescence in real time while the samples are subjected to thermal cycling. The thermal cycling device 32 includes a flat top 34, a depending heat sink 36 and a replaceable thermal block 38. Although shown only partially in FIGS. 2 and 3, the thermal block 38 takes the form of a generally rectangular plate having a flat top and a uniform thickness such that the flat top of the thermal block 38 is elevated above the level of the flat top 34 of the thermal cycling device 32. As shown most clearly in FIG. 3, the thermal block 38 has laterally projecting, bifurcated lugs 39 on each side thereof for securing it against thermal heating/cooling panels (not shown), and to the top 34 of the thermal cycling device 32 by bolts 40.

A heated cover plate 42, represented schematically by phantom lines in FIG. 2, is supported in the PCR instrument for vertical movement toward and away from the thermal block 38 and in angular registry therewith. The function of the cover plate is to press the microcard against the thermal block 38, while at the same time enabling operation of an optical scanning system (not shown) to read the samples in the respective sample chambers 14 of the microcard.

In accordance with the present invention, the handling device 30 includes a carrier having an apertured region with an array of holes corresponding in number and relative location with the array of reagent containing sample chambers in each of the micro-cards, means for retaining a micro-card on the carrier so that the transparent material of the microcard faces the apertured region with the reagent sample chambers aligned, respectively, with the holes in the apertured region, and so that the side of the micro-card opposite the transparent material is unobstructed at least throughout the array of reagent containing sample chambers. The handling device 30 additionally includes means for positioning the carrier and the micro-card retained thereon in relation to the PCR instrument.

In the illustrated embodiment, the handling device 30 defines a two-part carrier for the microcard 10, the two parts being a peripherally closed frame-like retention frame 44 and a carrier 46 having an array of holes 48 in a central apertured region, the holes corresponding in number and in location with the sample chambers 14 in the microcard 10.

As may be seen in FIGS. 2 and 3, the retention frame 44 includes a continuous peripheral wall 49 extending upwardly from a flared bottom 50 that seats against the flat top 34 of the thermal cycling device 32. A marginal flange 52 of the retention frame 44 extends inwardly from the peripheral wall 49 but elevated slightly above the flared bottom 50 that seats against the top 34. The marginal flange 52 defines a central opening 54 that is shaped to complement the peripheral shape of the thermal block 38 with a slight peripheral clearance between the inner edges of the marginal flange 52 and the outer edges of the thermal block 38. Also, as shown in FIG. 3, the thickness of the marginal flange 52 is less than that of the thermal block 38, so that when the flared bottom of the retention frame 44 is seated on the top 34 of the thermal cycling device 32, the top surface of the marginal flange 52 is lower than the top surface of the thermal block 38 even though the marginal flange is slightly elevated above the seating flared bottom 50.

To retain the microcard 10 by the retention frame 44, both ends of the microcard 10 overlie a pair of tabs 56 that project from opposite inner edges of the marginal flange 52 of the retention frame 44. Except for those retained end portions that overlie the tabs 56, the entire bottom surface of the microcard 10 is exposed through the opening 54 defined by the inner edges of the marginal flange 52.

The carrier 46 is defined in substantial measure by a flat plate 58, in which the array of holes 48 are formed. A peripheral wall 60, of a depth to project both above and below the plate 58, extends about three sides of the plate 58, as shown in FIG. 2. On the fourth side, the wall 60 is continued as a skirt 62 depending from the plate 58. A recessed portion 64 on the fourth side of the plate 58, together with a complementing recessed portion 66 in the wall 49 of the retention frame 44, provides a window for observation of identifying indicia on the microcard 10 when the carrier 46 and the retention frame 44 are closed about the microcard;

The peripheral edge surfaces of the carrier 46 are shaped and sized to fit somewhat loosely into the peripheral wall 49 of the retention frame 44. When the carrier 46 and retention frame 44 are assembled about a microcard 10 in a manner to be described below, a pair of clips 68 on each of opposite sides of the carrier 46 engage in apertures 70 on opposite sides of the retention frame 44 to secure the assembly. The clips 68 may be released from the apertures 70 by distorting the retention frame of by inserting a tool, such as a small screw driver, through the apertures and flexing the clips to permit removal of the microcard 10 from the device 30.

In FIG. 4, the bottom of the carrier 46 is shown to include pairs of wedge-shaped projections 72 on the bottom marginal regions of the carrier plate 58, outside of the region containing the array of holes 48. One such pair of projections 72 is provided on each side of the carrier 46. Also, a single wedge-shaped projection 72 is located in the corner of the carrier 46 that receives the chamfered corner 11 of the microcard 10. The wedge-shaped projections 72 function as positioning ramps such that when the carrier 46 is inverted, as shown in FIG. 4, the microcard 10, also inverted, may be placed into the inverted carrier and guided against the bottom of the carrier plate 58 so that the raised tapered surfaces 22 on the microcard are coarsely aligned with the respective holes 48. The retention frame 44 is then inverted and pressed against the carrier 46 until the clips 68 on the carrier 46 engage in the apertures 70 in the retention frame 44. The microcard 10 is then secured within the handling device 30, but with freedom of movement within the device 30 limited by the carrier plate 58 on the top, by the marginal flange 52 in the retention frame 44 on the bottom, and by the positioning ramps on the wedge-shaped projections 72 on the peripheral edges of the microcard 10.

As shown in FIG. 2, the top of the carrier 46 is also provided with pairs of wedge-shaped ramp members 74, one such pair on each side of the plate 58. These ramp members cooperate with the heated cover plate 42 of the PCR instrument so that when the cover plate 42 is lowered against the assembled handling device 30 positioned on the thermal block 38, precise final positioning of the handling device and of the microcard will be obtained by cooperation of the carrier 46 with the heated cover plate 42, and by cooperation of the holes 48 in the carrier 46 with the raised tapered surfaces 22 on the microcard 10. In particular, the final position of the carrier will be determined by the camming action of the heated cover plate 42 on the ramp members 74 on the top of the carrier 46, and the final position of the microcard 10 will be determined by the camming action of the holes 48 on the raised tapered surfaces 22 of the microcard 10.

As mentioned above with reference to FIG. 3, the thickness of the marginal flange 52 is less than that of the thermal block 38, so that when the retention frame 44 is seated on the top 34 of the thermal cycling device 32, the top surface of the marginal flange is lower than the top surface of the thermal block 38. This difference in elevation between the top of the marginal flange 52 and the top surface of the thermal block 38 represents the amount of vertical freedom of movement that the microcard has in the handling device 30 when the carrier 46 and retention frame are initially closed on each other, and permits the relative vertical movement of the carrier 46 and microcard 10 needed to effect the cam action final positioning of the microcard. Also, movement of the marginal flange 52 away from the bottom of the microcard 10 ensures that only the thermal block is in contact with the bottom of the card and that there will be no interference with heat transfer between the thermal block 38 and the microcard 10.

The carrier 46 and retention frame 44 are preferably constructed of a polymer that is able to withstand the heat used in a typical thermal cycling process, e.g., about 60° to 100° C. Thus, the handling device 30 should be able to maintain its original shape even after multiple thermal cycling processes. The device 30, described herein by way of example, is intended to be reusable and able to substantially maintain its shape after 50 or more hours of thermal cycling. A shelf life of about 5 years would also be expected. Materials that may be used for construction of the device 30 include polymers, plastics, glass, ceramics, metals, or others known in the art that are able to withstand the thermal cycling process. Furthermore, the handling device 30 of this invention may be manufactured in a variety of ways known in the art, including injection molding, machining, or metal stamping methods.

In FIGS. 5A and 5B, a microcard, representing a variant of the microcard 10 of FIGS. 1A and 1B, is designated generally by the reference number 80. As shown, the microcard 80 contains three hundred and eighty-four (384) sample chambers 82 connected with a fill port 84 via a network 86 of passageways, but may contain fewer chambers, such as ninety-six (96) chambers, for example. Also, the illustrated embodiment has only one fill port 84 but multiple fill ports may be used to facilitate loading of multiple reagents into the chambers 82.

As shown in the vastly enlarged fragmentary cross-section of FIG. 5B, the sample chambers 82 and network 86 of passageways are molded or otherwise formed as embossments in a top layer 88 of pliable and transparent plastic film. A bottom layer 90 of plastic lined or coated aluminum foil is suitably secured to the bottom of the top layer 88 by adhesives, for example, after an analyte-specific reagent is placed in each chamber 82 as described above with reference to the microcard 10. The combined thickness of the two layers 88 and 90 in areas of the microcard 80, other than areas occupied by the chambers 82 and network 86 of passageways, is on the order of less than 0.5 mm. The area occupied by the sample chambers 82 and passageway network 86 is about 11 cm×6.8 cm or essentially the same as the outside dimensions of the microcard 10 of FIGS. 1A and 1B. However, a peripheral margin 87 enlarges the total area of the microcard 80 to about 12.6 cm×8.4 cm. Because of the extreme thinness of the microcard 80 and the materials from which it is formed, the microcard 80 is both flexible and inclined to deformation from a flat, planar configuration.

As shown in FIG. 5A, pairs of through-holes 92 and 94 are located in the margin 87 at opposite ends of the microcard 80 outside of the area or region containing the chambers 82 and the passageway network 86. A single through hole 96 is located in the margin 87 on one side of the microcard. The function of the through-holes 92, 94, and 96 will be described in more detail below.

In accordance with the present invention, a device for handling PCR microcards of the type shown in FIGS. 5A and 5B is provided by a carrier having an apertured region with an array of holes corresponding in number and relative location with the array of sample chambers in each of the microcards, the carrier comprising a frame member including the apertured region, and pins projecting from the plate member outside of the apertured region to engage in through-holes formed in marginal portions of the microcard outside the array of sample chambers.

In the embodiment illustrated in FIGS. 6A–11 of the drawings, a handling device for the microcard 80 is designated generally by the reference number 100 and includes a carrier frame 102, a compression pad 104, alignment pins 106, and 112, and stacking pins 108 and 110. The carrier frame 102 provides the supporting structure of the handling device 100, is fabricated from a heat resistant polymer, and is sized to be similar in overall area dimensions of the microcard 80. As shown in FIG. 6B, the carrier frame 102 has a raised region 114 on the top side and a recessed region 116 on the bottom side thereof surrounded by a margin 118 generally complementing the margin 87 of the microcard 80. The recessed region 116 is apertured to include a total of three hundred eighty-four (384) holes 119, each preferably 3.0 mm in diameter, that penetrate through the thickness of the carrier frame to expose all 384 sample chambers 82 in the microcard 80 to the optical system of a PCR instrument of the type identified above.

To ensure thermal insulation and to provide good contact between the microcard 80 and a thermal cycling block to be described below, the silicone rubber compression pad 104 is situated in the recessed region 116 and to be positioned between the carrier frame 102 and the microcard 80 in use. The compression pad 104 also has three hundred and eighty four holes 122 aligned to the holes 119 in the carrier frame so not to obstruct the sample wells from the optics of the PCR instrument. The compression pad 104 is bonded to the recessed region on the underside of the carrier frame and becomes an inseparable part of the handling device 100.

On the underside of the carrier frame 102 in proximity to where the microcard fill port 84 will be located in use, the recessed region 118 is formed with a semi-circular raised region or ledge 124. The compression pad 104 is provided with a complementary semi-circular tab extension 126 located to be positioned on the ledge 124 when the compression pad 104 is secured in the recessed region 118. A combination of the raised ledge 124 and the tab extension 126 functions to ensure that more pressure is applied to the fill port region when the heated cover of the PCR instrument is lowered. A higher compressive force around the region of the fill port 84 prevents samples from leaking from the microcard via the fill port that is sealed with an adhesive tape (not shown).

To secure the microcard 80 to the underside of the carrier frame 102 and against the compression pad 104, and for positioning and aligning the microcard 80 in the PCR instrument, the pins 106, 108 110, and 112 protrude from the bottom of the carrier frame 102 in the outer marginal edges 118. When assembling the microcard 80 to the handling device 100, the pins 106 and 112 are inserted into two similarly positioned holes 92 in the microcard 80. A close press fit between the pins 106 and 112 and the holes 92 ensure proper alignment of the microcard with the card carrier frame 102. The press fit also prevents the microcard from separating from the card carrier during transport and handling. The two other pins 108 and 110 protrude from the underside of the card carrier and these pins, together with the two alignment pins 106 and 112, function as legs and provide a means for stacking multiple handling devices 100 with microcards assembled to them. The pins 108 and 110 also augment retention of the microcard 80 to the bottom of the carrier frame 102.

In FIGS. 7–11, a thermal block 130 for use with the handling device 100 is illustrated. Like the thermal block 38 described above with reference to FIGS. 2 and 3, the thermal block 130 has a flat top surface 132 and bifurcated attachment lugs along each side thereof for attachment by bolts to the top 34 of the thermal cycling device 32 in the same manner as the thermal block 38. The thermal block 130, however, is formed with at tapered holes 136, 138, and 140, at least two of which (138 and 140) are positioned to align with the pins 106 and 112, respectively, on the carrier frame 102 of the handling device 100. Thus, when the handling device, with the microcard 80 attached, is lowered onto the thermal block 130, the handling device 100 and the attached microcard 80 will be located precisely relative to the thermal block, and, more importantly, with the optical system of the PCR instrument.

In accordance with the present invention, the microcards 10 and 80 and the respective handling devices 30 and 100 are assembled in PCR processing kits, each such kit including at least one handling device 30, 100 and a supply of microcards 10, 80. A kit for use with PCR instrument model 7900HT sold by Applied Biosystems of Foster City, Calif., for example, would additionally include the appropriate thermal block 38 or 130, depending on whether the kit includes microcards 10 or 80. Other kits might include microcards filled with reagents of a supplier's design or custom reagents ordered by a customer. The appropriate handling device would be included with the filled microcards.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A device for handling at least one PCR substrate member in relation to a PCR instrument, the substrate member having an array of sample chambers closed by a translucent material on one side thereof, the device comprising:

a carrier having an apertured region with an array of holes substantially aligning with the array of sample chambers; and a retention frame having an opening at least as large as the array of sample chambers and being fitted to the carrier to retain the substrate member in relation to the carrier, wherein the carrier is constructed to contact the peripheral edge of the substrate member, and wherein the substrate member comprises a microcard.

2. The device of claim 1, wherein the retention frame is configured to at least partially surround the periphery of the substrate member.

3. The device of claim 2, wherein the retention frame is configured to surround at least two sides of the periphery of the substrate member.

4. The device of claim 1, wherein the carrier comprises a carrier plate including the apertured region.

5. The device of claim 4, wherein the carrier comprises inclined ramps on the bottom of the carrier plate to engage and guide edges of the substrate member upon relative movement of the carrier plate and substrate member toward each other.

6. The device of claim 1, wherein the retention frame includes a planar base and an inwardly extending marginal flange for seating the device on a flat surface of a thermal cycling device of the PCR instrument.

7. The device of claim 6, wherein the marginal flange is engageable with opposite edges of the substrate member.

8. The device of claim 6, wherein the marginal flange includes inwardly extending tabs to engage one end of the substrate member.

9. The device of claim 6, wherein the marginal flange defines the opening in the retention frame.

10. The device of claim 6, wherein the opening defined by the marginal flange is shaped to complement with clearance, the peripheral shape of a thermal black having a substrate member engaging surface elevated above the flat surface of the thermal cycling device.

11. The device of claim 10, further comprising raised, tapered surfaces aligned with each of the sample chambers and engageable in respective holes of the carrier.

12. The device of claim 1, further comprising inclined ramps on the top of the carrier plate engageable by edges of a heated cover plate of the PCR instrument to position the carrier plate and substrate member during operation of the instrument.

13. The device of claim 1, wherein the carrier comprises a side surface having a structure configured to be carried.

14. The device of claim 13, wherein the structure is configured to be carried by a robot.

15. A device for handling at least one substrate member in relation to a thermal cycling device, the substrate member having an array of sample chambers configured to permit optical detection through at least a first side thereof, the device comprising:

a carrier having an apertured region with an array of holes substantially aligning with the array of sample chambers; and a retention frame having an opening at least as large as the array of sample chambers and being fitted to the carrier to retain the substrate member in relation to the carrier, so that the side of the substrate member opposite the first side directly contacts a top surface of a thermal block of the thermal cycling device, wherein the carrier is constructed to contact the peripheral edge of the substrate member.

16. The device of claim 15, wherein the carrier comprises inclined ramps on the bottom of the carrier plate to engage and guide edges of the substrate member upon relative movement of the carrier plate and substrate member toward each other.

17. The device of claim 15, wherein the substrate member comprises a microcard.

18. The device of claim 15, wherein the carrier comprises a side surface having a structure configured to be carried.

19. The device of claim 18, wherein the structure is configured to be carried by a robot.

20. A device for handling at least one PCR substrate member in relation to a thermal cycling device, the substrata member having an array of sample chambers closed by a translucent material on one side thereof, the device comprising:

a carrier comprising a plate member having an apertured region with an array of holes substantially aligning with the array of sample chambers, the plate member further having a plurality of projections extending from the plate member, the substrate member defining through-holes in marginal portions thereof outside the sample chambers, the projections of the plate member projecting from the plate member to engage and pass through the through-holes; and a thermal block attachable to the thermal cycling device, the thermal block defining a top surface on which the substrate member may be placed in direct contact therewith, the thermal block defining a plurality of holes for receiving the projections of the plate member therein.

21. The device of claim 20, wherein the plate member defines a bottom recess containing the apertured region and a peripheral margin from which the projections project.

22. The device of claim 21, further including a compression pad in the bottom of the recess, the compression pad including an array of holes substantially aligning with the holes in the carrier plate.

23. The device of claim 22, wherein the carrier plate projections comprise pins.

24. The device of claim 23, wherein the pins are cylindrical.

25. The device of claim 20, wherein the holes of the thermal block are tapered.

26. The device of claim 20, wherein the substrate member comprises a microcard.

27. The device of claim 20, wherein the carrier comprises a side surface having a structure configured to be carried.

28. The device of claim 27, wherein the structure is configured to be carried by a robot.

29. A device for handling at least one PCR substrate member in relation to a PCR instrument, the substrate member having an array of sample chambers closed by a translucent material on one side thereof, the device comprising:

a carrier having an apertured region with an array of holes substantially aligning with the array of sample chambers; and a retention frame having an opening at least as large as the array of sample chambers and being fitted to the carrier to retain the substrate member in relation to the carrier, wherein the carrier is constructed to contact the peripheral edge of the substrate member, and wherein the carrier and the retention frame are configured to retain the substrate member therebetween.

30. The device of claim 29, wherein the retention frame is configured to at least partially suround the periphery of the substrate member.

31. The device of claim 30, wherein the retention frame is configured to surround at least two sides of the periphery of the substrate member.

32. The device of claim 29, wherein the carrier comprises a carrier plate including the apertured region.

33. The device of claim 32, wherein the carrier comprises inclined ramps on the bottom of the carrier plate to engage and guide edges of the substrate member upon relative movement of the carrier plate and substrate member toward each other.

34. The device of claim 29, wherein the retention frame includes a planar base and an inwardly extending marginal flange for seating the device on a flat surface of a thermal cycling device of the PCR instrument.

35. The device of claim 34, wherein the marginal flange is engageable with opposite edges of the substrate member.

36. The device of claim 34, wherein the marginal flange includes inwardly extending tabs to engage one end of the substrate member.

37. The device of claim 34, wherein the marginal flange defines the opening in the retention frame.

38. The device of claim 34, wherein the opening defined by the marginal flange is shaped to complement with clearance, the peripheral shape of a thermal block having a substrate member engaging surface elevated above the flat surface of the thermal cycling device.

39. The device of claim 38, further comprising raised, tapered surfaces aligned with each of the sample chambers and engageable in respective holes of the carrier.

40. The device of claim 29, further comprising inclined ramps on the top of the carrier plate engageable by edges of a heated cover plate of the PCR instrument to position the carrier plate and substrate member during operation of the instrument.

41. The device of claim 29, wherein the carrier comprises a side surface having a structure configured to be carried.

42. The device of claim 41, wherein the structure is configured to be carried by a robot.

43. The device of claim 29, wherein the substrate member comprises a microcard.

* * * * *